United States Patent
Beckman et al.

(10) Patent No.: US 7,271,286 B2
(45) Date of Patent: Sep. 18, 2007

(54) CARBOXYLATION OF AROMATIC HYDROCARBONS TO PRODUCE AROMATIC CARBOXYLIC ACIDS

(75) Inventors: Eric J. Beckman, Aspinwall, PA (US); Pradip Munshi, Pittsburgh, PA (US)

(73) Assignee: The University of Pittsburgh - of the Commonwealth System of Higher Education, Pittsburgh, PA (US)

( * ) Notice: Subject to any disclaimer, the term of this patent is extended or adjusted under 35 U.S.C. 154(b) by 303 days.

(21) Appl. No.: 11/038,795

(22) Filed: Jan. 20, 2005

(65) Prior Publication Data

US 2005/0187404 A1 Aug. 25, 2005

Related U.S. Application Data

(60) Provisional application No. 60/538,300, filed on Jan. 22, 2004.

(51) Int. Cl.
*C07C 51/16* (2006.01)
(52) U.S. Cl. ..................... 562/408; 562/412
(58) Field of Classification Search .............. None
See application file for complete search history.

(56) References Cited

U.S. PATENT DOCUMENTS

| 1,866,717 A | 7/1932 | Meyer et al. | |
|---|---|---|---|
| 2,833,816 A | 5/1958 | Saffer et al. | 260/524 |
| 3,138,626 A | 6/1964 | Calfee et al. | 260/488 |
| 5,103,933 A | 4/1992 | Huff et al. | 182/18 |

FOREIGN PATENT DOCUMENTS

EP 00706987 4/1996

OTHER PUBLICATIONS

Weissermel, K.; Arpe, H-J.; Industrial Organic Chemistry, 3rd edition; 1997; 392; Weinheim, Ger.
Ogata, Y.; Hojo, M. ; Morikawa, M.; J. Org. Chem.; 1960; vol. 25; 2082-7.
Ogata, Y.; Tsuchida, M.; Muramoto, A.; J. Am. Chem. Soc.; 1957; vol. 79; 6005-6008.
Olah, G. A.; Török, B.; Joschek, J. P.; Bucsi, I.; Esteves, P. M.; Rasul, G.; Prakash, G. K. S.; J. Am. Chem. Soc.; 2002; vol. 124; 11379-11391.
Sugimoto, H.; Kawata, I.; Taniguchi, H.; Fujiwara, Y.; Journal of Organometallic Chemistry; 1984; vol. 266 ; C44-C46; The Netherlands.

*Primary Examiner*—Sikarl A. Witherspoon
(74) *Attorney, Agent, or Firm*—Himanshu Vyas

(57) ABSTRACT

Aromatic carboxylic acids are produced by reacting a Lewis acid: $CO_2$ complex with aromatic hydrocarbons. The complex can be created by incubating a Strong Lewis acid and $CO_2$ and forming a composition consisting essentially of $CO_2$, strong Lewis acid, and Lewis acid: $CO_2$ complex. Carboxylation of aromatic hydrocarbons to produce aromatic carboxylic acids using the composition and method in accordance with this invention provides improved yields without the use of finely divided aluminum or zinc.

10 Claims, No Drawings

CARBOXYLATION OF AROMATIC HYDROCARBONS TO PRODUCE AROMATIC CARBOXYLIC ACIDS

This application claims the benefit of the provisional U.S. Application Ser. No. 60/538,300, filed Jan. 22, 2004.

BACKGROUND OF THE INVENTION

Aromatic carboxylic acids such as benzene dicarboxylic acids, naphthalene dicarboxylic acids, and others are commercially valuable as the raw materials for manufacture of polyesters which are used to manufacture fibers, films, resins, and many other useful articles. Aromatic carboxylic acids can be produced via liquid phase oxidation of aromatic hydrocarbon feedstock. U.S. Pat. No. 2,833,816, incorporated by reference herein, discloses liquid phase oxidation of xylene isomers into corresponding benzene dicarboxylic acids in the presence of bromine using a catalyst having cobalt and manganese components. As described in U.S. Pat. No. 5,103,933, liquid phase oxidation of dimethylnaphthalenes to naphthalene dicarboxylic acids can also be accomplished in the presence of bromine and a catalyst having cobalt and manganese components.

As used herein, "aromatic hydrocarbon" preferably means a molecule composed predominantly of carbon atoms and hydrogen atoms, and having one or more aromatic ring, particularly benzene, toluene, dimethyl benzenes, naphthalenes, methyl naphthalenes and dimethyl naphthalenes. Aromatic hydrocarbons suitable for liquid-phase oxidation to produce aromatic carboxylic acid generally comprise an aromatic hydrocarbon having one or more substituent groups, at least one of which is oxidizable to a carboxylic acid group. As used herein, "aromatic carboxylic acid" means an aromatic hydrocarbon having one or more substituent groups, at least one of which is a carboxyl group.

In a typical liquid phase oxidation process, an aromatic hydrocarbon feedstock and a solvent are reacted with an oxidant gas in the presence of a bromine promoter and catalyst. Typically, the solvent comprises a $C_1$-$C_8$ monocarboxylic acid, for example acetic acid, benzoic acid, or mixtures thereof with water. Typically, air is used as the oxidant gas. The particular aromatic hydrocarbon used depends upon the desired aromatic carboxylic acid. For example, in the production of benzene dicarboxylic acids, the corresponding xylene isomer is used as aromatic hydrocarbon feedstock. Ortho-xylene is oxidized to produce phthalic acid, meta-xylene is oxidized to produce isophthalic acid, and para-xylene is oxidized to produce terephthalic acid.

Aromatic carboxylic acid product obtained from a liquid phase oxidation process may be subjected to a subsequent purification process. The purification process may include treating the aromatic carboxylic acid product with hydrogen gas in the presence of a hydrogenation catalyst.

The presence of isomers or other species in an Aromatic hydrocarbon feedstock can impact a particularly desired oxidation process. Costly separation procedures are often employed to reduce the presence of such isomers or other species in an aromatic hydrocarbon feedstock for commercial oxidation processes. For example, meta-xylene may be separated from para-xylene to form a para-xylene feed of sufficient purity for use in commercial liquid phase oxidation processes for the production of terephthalic acid. Such separation procedures can be difficult and costly and, consequently, the supply of such aromatic hydrocarbon feedstocks can be costly. It would be advantageous to employ alternative processes for producing aromatic carboxylic acids from more easily obtainable aromatic hydrocarbon feedstocks.

U.S. Pat. No. 1,866,717 to Meyer, et al., incorporated by reference herein, discloses a method of producing aromatic carboxylic acids by allowing $CO_2$ to react with an aromatic hydrocarbon in the presence of aluminum chloride. Yields from the reactions described by Meyer, et al., (based on $AlCl3$) are very low, ranging from about 5% at atmospheric pressure to about 15% or 20% at 200 atmospheres (20.27 Mpa).

U.S. Pat. No. 3,138,626 to Calfee, et al., incorporated by reference herein, discloses the carboxylation of aromatic hydrocarbons with $CO_2$, aluminum chloride, and finely divided aluminum or zinc to produce aromatic carboxylic acids. Addition of zinc or aluminum metal in finely divided form increases the yield of carboxylated product formed during aluminum chloride catalyzed carboxylation of aromatic hydrocarbons by $CO_2$ compared to the yield in accordance with Meyer, et al. Addition of finely divided aluminum metal results in yields of carboxylated product (based on $AlCl_3$) of about 23% at atmospheric pressure and from about 55% to about 60% at about 200 atmospheres of pressure (20.27 Mpa). Unfortunately, finely divided aluminum or zinc is costly. It would be advantageous to achieve an increased yield of carboxylated product without adding finely divided aluminum or zinc.

In processes for the carboxylation of aromatic hydrocarbons, a reaction mixture of aromatic hydrocarbon feedstock and a Lewis acid are introduced into a reactor and the reactor is then pressurized with $CO_2$. Zinc or aluminum powder, if used, would be added to the reaction mixture before pressurizing the reactor with $CO_2$. We have found that, surprisingly, premixing $CO_2$ and the Lewis acid significantly improves yield of carboxylated product without the addition of zinc or aluminum powder.

SUMMARY OF THE INVENTION

This invention provides a method of producing aromatic carboxylic acid comprising the steps of incubating $CO_2$ and a strong Lewis acid at incubation conditions to produce a resulting mixture; and reacting, at effective reaction pressure and effective reaction temperature, aromatic hydrocarbon with the resulting mixture. Incubation of the $CO_2$ and strong Lewis acid is preferably conducted in the absence of the aromatic hydrocarbon. Incubation conditions preferably include incubation pressure ranging from about 1 to about 50 MPa, more preferably ranging from about 5 to about 20 MPa, and at incubation temperature ranging from about 300 to about 500K, more preferably ranging from about 320 to about 400K. Effective reaction pressure preferably ranges from about 4 to about 15 MPa and effective reaction temperature preferably ranges from about 330 to about 390K.

This invention also provides a method for producing aromatic carboxylic acid comprising reacting a composition consisting essentially of $CO_2$, strong Lewis acid, and Lewis acid: $CO_2$ complex with an aromatic hydrocarbon at effective reaction pressure and effective reaction temperature. Effective reaction pressure preferably ranges from about 4 to about 15 MPa and effective reaction temperature preferably ranges from about 330 to about 390K. The composition is preferably formed by incubating $CO_2$ and strong Lewis acid under incubation conditions. Incubation conditions prefer ably include incubation pressure ranging from about 1 to about 50 MPa, more preferably ranging from about 5 to about 20 MPa, and incubation temperature preferably ranging from about 300 to about 500K, more preferably ranging from about 320 to about 400K.

This invention also provides a composition for the production of aromatic carboxylic acids, the composition consisting essentially of $CO_2$; strong Lewis acid; and Lewis acid: $CO_2$ complex. Preferably the Lewis acid: $CO_2$ complex is formed by incubating the $CO_2$ and the strong Lewis acid under incubation conditions. Incubation of the $CO_2$ and the strong Lewis acid under incubation conditions is preferably conducted in the absence of aromatic hydrocarbons. Incubation conditions preferably includes incubation pressure ranging from about 1 to about 50 MPa, more preferably ranging from about 5 to about 20 MPa, and preferably includes incubation temperature ranging from 300 to about 500K, more preferably ranging from about 320 to about 400K.

DESCRIPTION OF THE PREFERRED EMBODIMENT(S)

In a process for the carboxylation of aromatic hydrocarbons, a reaction mixture of aromatic hydrocarbon feedstock and a Lewis acid are introduced into a reactor and the reactor is then pressurized with $CO_2$. Zinc or aluminum powder, if used, would be added to the reaction mixture before pressurizing the reactor with $CO_2$. We have found that, surprisingly, premixing $CO_2$ and the Lewis acid before introducing aromatic hydrocarbon feedstock significantly improves yield of carboxylated product without the addition of zinc or aluminum powder.

The carboxylation of aromatic hydrocarbons in accordance with this invention can be conducted by mixing a Lewis acid with $CO_2$ before adding a chosen aromatic hydrocarbon feedstock. Suitable aromatic hydrocarbons for the instant invention generally comprise an aromatic hydrocarbon capable of bonding with one or more carboxyl groups. The particular aromatic hydrocarbon chosen will vary according to the carboxylated aromatic hydrocarbon product desired. For example, benzene would be a preferred aromatic hydrocarbon feedstock to produce benzoic acid, benzene dicarboxylic acids, and benzene tricarboxylic acids. Toluene would be a preferred aromatic hydrocarbon feedstock to produce toluic acid. For further example, naphthalene would be a preferred aromatic hydrocarbon feedstock for a naphthoic acid product or a naphthalene polycarboxylic acid product. Similarly, for a desired alkyl-aromatic carboxylic acid product, the preferred hydrocarbon feedstock would be the corresponding alkyl-aromatic hydrocarbon.

Strong Lewis acids are suitable for use in the reaction of this invention. As used herein, "strong Lewis acid" is preferably a Lewis acid with acidity sufficient to form an acid: $CO_2$ complex. As used herein, "acid: $CO_2$ complex" means a Lewis acid bonding with at least one $CO_2$ molecule. Examples of strong Lewis acids include aluminum chloride, sodium aluminum chloride, titanium chloride, zinc triflate, zinc acetate, tin chloride, molybdenum chloride, and others capable of forming an acid: $CO_2$ complex.

Molar ratio of $CO_2$ to Lewis acid present in accordance with this invention is preferably greater than 1:1, more preferably at least 2:1. Generally, increasing the ratio of moles of $CO_2$ to moles Lewis acid speeds up the formation of the acid: $CO_2$ complex. Typically, ratios in the range from about 5:1 to about 30:1 are most preferred.

Lewis acid and $CO_2$ are mixed together and allowed to incubate under incubation conditions. "Incubation conditions" as used herein means a selection of incubation period, incubation temperature and incubation pressure effective for substantial formation of acid: $CO_2$ complex. Other things being equal, the three properties, incubation period, incubation temperature and incubation pressure, for a given Lewis acid typically are interrelated, such that an increase in one or two of the properties allows decrease of the remaining one or two properties for substantial complex formation, and conversely, a decrease in one or two of the properties facilitates an increase of one or both of the remaining properties.

Preferably, the incubation period is at least about 15 minutes, more preferably at least about 30 minutes, more preferably at least about 45 minutes, and is preferably less than about 120 minutes, more preferably less than about 90 minutes. Most preferably, the incubation time is about 60 minutes.

Preferably, incubation pressure is at least about 1 MPa, more preferably at least about 5 MPa. Preferably, incubation pressure is not more than about 50 MPa, more preferably not more than about 20 MPa. Most preferably, incubation pressure is about 10 MPa. Incubation temperature is preferably at least about 300K, more preferably at least about 320K. Preferably, incubation temperature is not more than about 500K, more preferably not more than about 400K. Incubation temperature is most preferably about 350K.

After the incubation period, the incubated mixture is combined with a chosen aromatic hydrocarbon feedstock. Carboxylation of the aromatic hydrocarbon is conducted at an effective reaction pressure and effective reaction temperature. By "effective reaction pressure" and "effective reaction temperature" is meant a pressure and temperature, respectively, sufficient to promote reaction between the acid: $CO_2$ complex and the chosen aromatic hydrocarbon. Effective reaction pressure and effective reaction temperature will vary depending upon the particular aromatic hydrocarbon feedstock and the particular Lewis acid used. Other things being equal, effective reaction temperature and effective reaction pressure for a given Lewis acid typically are interrelated, with higher temperatures generally allowing use of lower pressures for carboxylation, and conversely, higher pressures facilitating reduced temperature requirements.

Ratio of aromatic hydrocarbon present in the carboxylation reaction to Lewis acid used can range from about 1:1 to about 20:1, preferably from about 2:1 to about 10:1.

Preferably, effective reaction pressure is at least about 2.0 MPa, more preferably at least about 4.0 MPa, more preferably at least about 6.0 MPa. Effective reaction pressure is preferably no more than about 20 MPa, more preferably no more than about 15 MPa, more preferably no more that about 7.0 MPa. Effective reaction pressure most preferably is about 6.9 MPa. Effective reaction temperature is preferably at least about 310K, more preferably at least about 330K. Preferably, effective reaction temperature is no more than about 410K, more preferably no more than about 390K. Effective reaction temperature most preferably ranges from about 350K to about 370K. Conducting the carboxylation reaction at more preferred effective reaction pressures and effective reaction temperatures provides better balance between yield of carboxylated product and severity of reaction conditions than operation under less preferable reaction conditions.

The reactants are subjected to an intimate contacting means, for example stirring, shaking, or otherwise contacting the reactants for selected reaction time. The reaction is conducted for a time period sufficient to produce the desired yield of carboxylated. For example, the reaction can be conducted for a time period such that the detriment of incremental increase in reaction time outweighs the benefit of any resulting increase in yield of aromatic carboxylic acid product. The reaction time will vary depending upon the particular Lewis acid used, aromatic hydrocarbon used, and reaction conditions used and upon the desired yield and can range from about 10 minutes to about 30 hours.

For a batch processes, the reaction is preferably allowed to continue for at least about 10 hours, more preferably at least about 14 hours. The reaction time is preferably no more that about 30 hours, more preferably no more than about 24 hours.

Most preferably the reaction time is about 20 hours. For a continuous or semi-continuous process, preferred residence times would be analogous to the preferred reaction times for batch processes.

The aromatic carboxylic acid product is produced in a salt form and can be recovered through known methods, for example acidic water treatment of the reaction mixture. The aromatic carboxylic acid product can be separated from the reaction mixture using known separation techniques, for example, precipitation, membrane separation, solvent extraction, distillation or other separation techniques.

The invention is further described in the following examples, which are presented for purposes of illustration, not limitation. Reagents were handled under inert atmosphere to avoid any loss of Lewis acid activity and all materials were obtained from Aldrich Chemical Company and used as received.

EXAMPLE A

Several reactions in accordance with this invention were run using varying temperatures, pressures, and reaction times. In each of Runs 1-13, a weighed amount of anhydrous $AlCl_3$ corresponding to the indicated molar amount of anhydrous $AlCl_3$ was added to a 31 mL high pressure reaction vessel with a Teflon stir bar constructed at the University of Pittsburgh and has a useful operating pressure range from 0 to about 50 MPa at temperatures below 423K. The vessel was sealed and $CO_2$ was added using a Haskell Gas Booster compressor until the vessel reached the indicated pressure. Stirring at about 400 rpm was started and the temperature was raised to 353K. The contents were allowed to incubate for 1 hour. At the end of the incubation period, excess toluene (approximately 4 times on a molar basis with respect to $AlCl_3$) was added using a high pressure syringe pump from High Pressure Equipment Co., Erie, Pa. The reaction was allowed to run for the indicated number of hours at the temperature and pressure listed, after which it was stopped via the slow introduction of 5 mL of 1M HCl. The vessel was then slowly depressurized while cooling to room temperature. Yield of toluic acid (relative to moles of $AlCl_3$) was measured. The results are included in Table I below.

TABLE I

| Run # | $AlCl_3$ mmol | Pressure MPa | Reaction Time Hours | Reaction Temp. K. | Yield % |
|---|---|---|---|---|---|
| 1 | 4.81 | 1.38 | 18 | 353 | 12 |
| 2 | 5.6 | 3.45 | 18 | 353 | 41 |
| 3 | 3.9 | 5.52 | 18 | 353 | 63 |
| 4 | 4.21 | 6.90 | 18 | 353 | 83 |
| 5 | 4.80 | 6.90 | 18 | 300 | 10 |
| 6 | 4.00 | 6.90 | 18 | 313 | 35 |

TABLE I-continued

| Run # | $AlCl_3$ mmol | Pressure MPa | Reaction Time Hours | Reaction Temp. K. | Yield % |
|---|---|---|---|---|---|
| 7 | 5.11 | 6.90 | 18 | 323 | 57 |
| 8 | 4.43 | 6.90 | 18 | 373 | 85 |
| 9 | 4.53 | 6.90 | 18 | 423 | 40 |
| 10 | 4.11 | 6.90 | 5 | 353 | 27 |
| 11 | 3.96 | 6.90 | 15 | 353 | 60 |
| 12 | 4.20 | 6.90 | 20 | 353 | 82 |
| 13 | 4.66 | 6.90 | 30 | 353 | 80 |

The results shown in Table I show that the method of this invention can be used to achieve higher yields at significantly lower pressure, without using zinc or aluminum powder, than the results achieved according to Calfee et al., (U.S. Pat. No. 3,138,626).

EXAMPLE B

Several additional reactions were conducted using various Lewis acids. Runs 14-23 were conducted in the same manner as Runs 1-13 with the reaction conducted at a pressure of 5.9 MPa, temperature of 353K, and time of 18 hours. The results are shown in Table II below.

TABLE II

| Run # | Lewis Acid | Mmol Used | % Yield |
|---|---|---|---|
| 14 | $AlCl_3$ | 5.37 | 80 |
| 15 | $NaAlCl_4$ | 4.66 | 60 |
| 16 | $TiCl_4$ | 3.34 | 71 |
| 17 | $Ti(OEt)_4$ | 5.22 | 25 |
| 18 | $Zn(OTf)_2$ | 5.10 | 30 |
| 19 | $Zn(OAc)_2$ | 5.62 | 55 |
| 20 | $CuBr_2$ | 4.91 | 50 |
| 21 | $SnCl_4$ | 5.00 | 81 |
| 22 | $MoCl_5$ | 4.42 | 76 |

The results in Table II show that the method of this invention resulted in appreciable yield for a variety of Lewis Acids without adding zinc or aluminum powder and at significantly lower pressures than the method of Calfee et al.

That which is claimed is:

1. A method of producing aromatic carboxylic acid, the method comprising the steps of:
   a) incubating $CO_2$ and a strong Lewis acid at incubation conditions to produce a resulting mixture; and
   b) reacting, at effective reaction pressure and effective reaction temperature, aromatic hydrocarbon with the resulting mixture.

2. The method of claim 1 wherein the step of incubating $CO_2$ and a strong Lewis acid at incubation conditions to produce a resulting mixture is conducted in the absence of the aromatic hydrocarbon.

3. The method of claim 1 wherein the step of incubating $CO_2$ and a strong Lewis acid at incubation conditions to produce a resulting mixture is conducted at incubation pressure ranging from about 1 to about 50 MPa and at incubation temperature ranging from about 300 to about 500 K.

4. The method of claim 1 wherein the step of incubating $CO_2$ and a strong Lewis acid at incubation conditions to produce a resulting mixture is conducted at incubation pressure ranging from about 5 to about 20 MPa and at incubation temperature ranging from about 320 to about 400K.

5. The method of claim 1 wherein the step of reacting, at effective reaction pressure and effective reaction temperature, aromatic hydrocarbon with the resulting mixture is conducted at effective reaction pressure ranging from about 4 to about 15 MPa and effective reaction temperature ranging from about 330 to about 390K.

6. A method for producing aromatic carboxylic acid, the method comprising reacting a composition consisting essentially of $CO_2$, strong Lewis acid, and Lewis acid:$CO_2$ complex with an aromatic hydrocarbon at effective reaction pressure and effective reaction temperature.

7. The method of claim 6 wherein the composition and aromatic hydrocarbon are reacted at an effective reaction pressure ranging from about 4 to about 15 MPa and an effective reaction temperature ranging from about 330 to about 390K.

8. The method of claim 6 further comprising the step of forming the composition by incubating $CO_2$ and strong Lewis acid under incubation conditions.

9. The method of claim 6 wherein the step of forming the composition by incubating $CO_2$ and strong Lewis acid under incubation conditions is conducted at incubation pressure ranging from about 1 to about 50 MPa and incubation temperature ranging from about 300 to about 500K.

10. The method of claim 6 wherein the step of forming the composition by incubating $CO_2$ and strong Lewis acid under incubation conditions is conducted at incubation pressure ranging from about 5 to about 20 MPa and incubation temperature ranging from about 320 to about 400K.

* * * * *